United States Patent [19]
Sato

[11] Patent Number: 5,964,587
[45] Date of Patent: Oct. 12, 1999

[54] BITE CONTROL POINT AND A METHOD TO FORM A PROJECTION ON TOOTH SURFACE

[76] Inventor: Mikio Sato, 11-6, Izumi-cho, Atsugi-shi, Kanagawa-ken, 243-0013, Japan

[21] Appl. No.: 09/154,245

[22] Filed: Sep. 16, 1998

[51] Int. Cl.⁶ ....................................... A61C 3/00
[52] U.S. Cl. ................................. 433/6; 128/861
[58] Field of Search .................... 433/6, 24, 214, 433/215, 8, 9, 5; 128/848, 861

[56] References Cited

U.S. PATENT DOCUMENTS

| | | | |
|---|---|---|---|
| 2,086,656 | 7/1937 | Woodward | 128/861 |
| 5,186,623 | 2/1993 | Breads et al. | 433/24 |
| 5,263,859 | 11/1993 | Kesling | 433/24 |
| 5,266,028 | 11/1993 | Adkisson | 433/24 |
| 5,645,420 | 7/1997 | Bergersen | 433/6 |

FOREIGN PATENT DOCUMENTS 2599686  1/1997  Japan .

*Primary Examiner*—Gene Mancene
*Assistant Examiner*—Pedro Philogene
*Attorney, Agent, or Firm*—Armstrong, Westerman, Hattori, McLeland & Naughton

[57] ABSTRACT

This invention is a ready-made bite control point which aims at easing the dentist to form the projections on the tooth side without a specialized tool and comprises a swelling to be fitted into a side hollow of a positioner for tooth-straightening employed in the dental treatment of open bite.

10 Claims, 4 Drawing Sheets

| SIZE (mm) | | (1) | (2) | (3) | (4) | (5) | (6) |
|---|---|---|---|---|---|---|---|
| B.C. POINTS FOR UPPER | LENGTH | 2.0-5.0 | 1.5-4.5 | 2.0-5.0 | 1.5-4.0 | 1.5-4.0 | 2.0-5.0 |
| | WIDTH | 1.5-5.0 | 1.5-3.0 | 1.5-5.0 | 1.5-4.0 | 1.5-4.0 | 2.0-8.0 |
| B.C. POINTS FOR LOWER | LENGTH | 1.5-4.5 | 1.5-4.5 | 2.0-5.0 | 1.5-3.5 | 1.5-3.5 | 1.5-3.0 |
| | WIDTH | 1.5-3.0 | 1.5-3.0 | 1.5-5.0 | 1.5-4.0 | 1.5-4.0 | 2.0-8.0 |

BITE CONTROL POINT AND A METHOD TO FORM A PROJECTION ON TOOTH SURFACE

FIELD OF THE INVENTION

This invention belongs to the field of implements employed in the dental treatment of the tooth-straightening to make right an irregular set of teeth, especially effective for the line of teeth uneven to the vertical direction.

BACKGROUND OF INVENTION

These days the increased patients have reported who are diagnosed as 'open bite' disease (a type of malocculation called anterior open bite) where the upper front teeth and the lower front teeth do not meet each other no matter how the upper back teeth and the lower back teeth bite well each other without a gap. To cure the open bite the dentist has to pull the unequal teeth a little to the level enough to fill the space between the upper front teeth and the lower front teeth out of the gem as well as keep the cured position after he/she moves the irregular teeth to the vertical direction so as to prevent the corrected row of teeth from getting back to the former unequal line. The prior orthodontia could cure the patients who have an irregular set of teeth, some of which lean outside and others incline inside using the implement of the metal braces to give a press to the horizontal direction so as to keep the corrected position of the moved teeth. Such a prior art is apparently useless for the remedy of 'open bite' where the teeth have to be moved to the vertical direction.

To treat the open bite the inventor has invented a new implement 'positioner' for fixing the improved line of teeth and also a novel method to anchor the 'positioner' at the right place in the mouth. As shown in FIG. 4 the positioner30 has depressions31 moulded into the shape of tooth line and hollows32 moulded to agree with the projections39 affixed on the back side of the cured teeth33,36. The depressions31 are deeper than the depth of teeth33,36 so that the space40 appears which prevents the positioner30 from pushing the tooth33 toward the direction of its root34 or pressing the tooth36 toward the direction of its root37. A part41 of the positioner30 is made of a rigider material, one end of it supports the upper gem35 and the other end bears the lower gem38 so as to keep the space40 open and prevent the positioner30 from pressing the treated teeth33,36 toward their root directions. In this invention a specialized tool is employed as shown in FIG. 5 the head51 of the tool50 is made of a material which does not react with the photo-synthetic resin in the photo-synthetic reaction but can let the light pass through so as to stiffen the photo-synthetic resin54 in the concave52 by causing the photo-synthetic reaction. The polycarbonate resin is a good choice for such a head51. A dentist can fill the concave52 with the loose photo-synthetic resin54 and handle the rod53 of the tool50 to position the head51 at the back side of the tooth36 adjusting to the appropriate place, usually 1 mm or 2 mm apart from the gem38 as the letter E indicates, then irradiate the beam of light toward the resin54 to harden it and form the projection39 on the back side of the tooth36.

SUMMARY OF THE INVENTION

The invention is a pre-manufactured bite control point to facilitate the dentist to form the projections on the tooth side without a speciallized tool. The ready-made bite control points can be attached easily on the side of the corrected teeth using adhesive, which will meet with the hollows of moulded 'positioner' to be installed ion the oral cavity.

The invention of claim 1 is a ready-made bite control point which has a swelling to be fitted into a side hollow of a positioner for tooth-straightening, and the invention of claim 2 is a said bite control point of claim 1 wherein the swelling has a slope at one edge which is gentler than that of the opposite side to make it easy to slide in the positioner in setting and to maintain the tightness between the positioner and the bite control points in use. The invention of claim3 is a method of forming a projection on tooth surface to be fitted into a side hollow of a positioner where said ready-made bite control point of claim 1 or 2 is attached to the tooth surface with adhesive.

DETAILED DESCRIPTION OF THE PREFERRED EMBODIMENTS

Figure 1A:
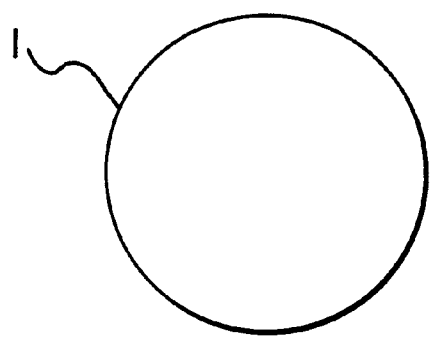
FIG. 1(a) is a plane figure and (b) is a side view, showing an embodiment of this invention.
Figure 1B:
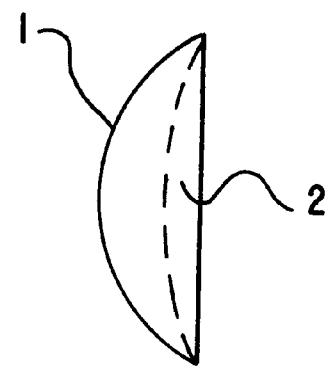
Figure 2A:
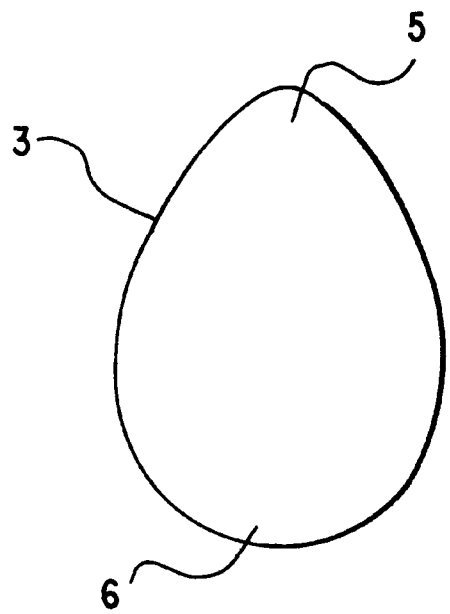
FIG. 2(a) is a plane figure and (b) is a side view, showing another embodiment of this invention.
Figure 2B:
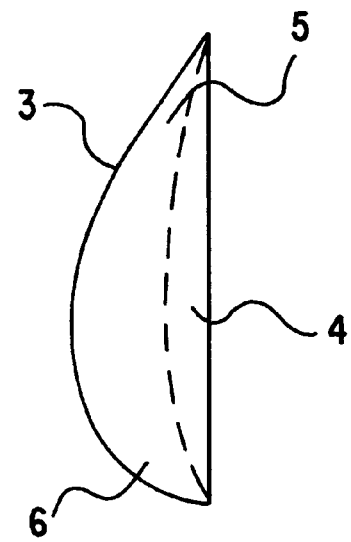

As shown in FIG. 1, the first embodiment of this invention is a round bite control point1 which is easy to be placed when a dentist tries to stick it with adhesive onto the tooth side because the circular shape of this embodiment is symmetrical and free from directivity. The dentist may place an edge of the embodiment1 on top or other edge on top instead. As shown in FIG. 2, another embodiment of this invention is a non-circular bite control point3 which makes it easy for the positioner to slide in against the projections of the bite control points when the positioner is set in the oral cavity because the tip part5, directing to the top of a tooth, is thinner and narrower than the opposite part6, directing to the root of a tooth.

A dentist can quite easily stick the above embodiments1,3 onto the appropriate site of the tooth in such a way as; (1) to etch the area for adhesion on the tooth side, (2) to wash and dry up there, (3) to put the adhesive on the surface2,4 of the bite control point1,3, (4) to press the surface2,4 for adhesion against the etched area of the tooth side, (5) to give irradiation in order to stiffen the adhesive if the adhesive photo-synthetic resin is selected.

Figures 3A, 3B:
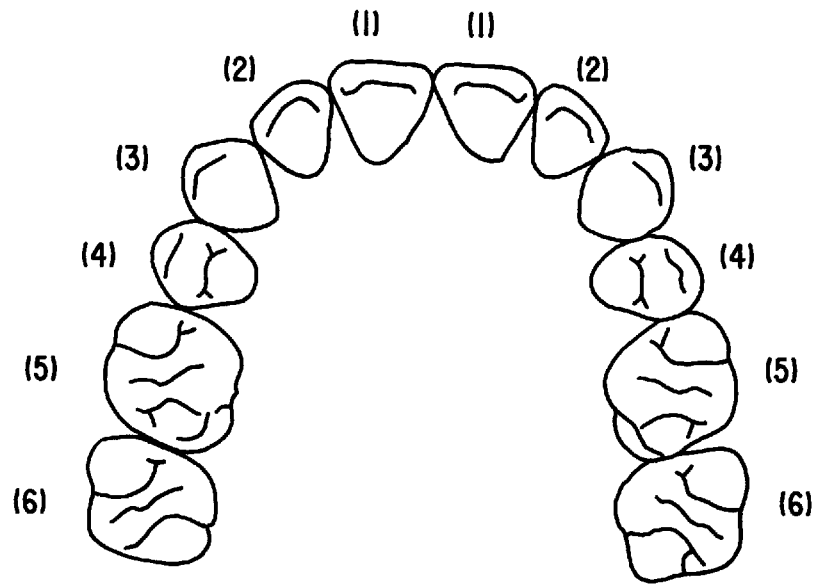
FIG. 3(a) is a sample of a toothprint and (b) indicates a sample of the size of the bite control points suitable for the standard Japanese people.
Figure 4A:
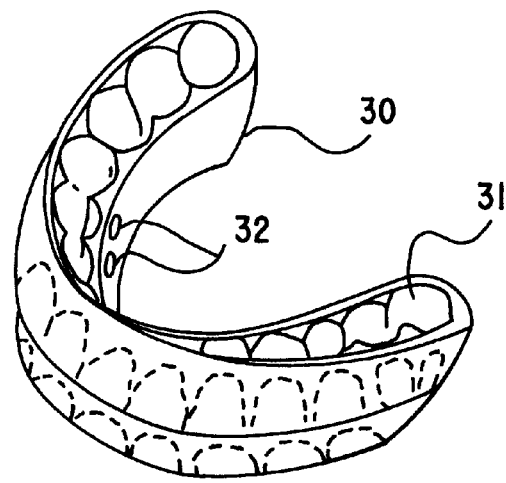
FIG. 4(a) is a squint showing a 'positioner' and (b) is a cross section showing the 'positioner' in use.
Figure 4B:
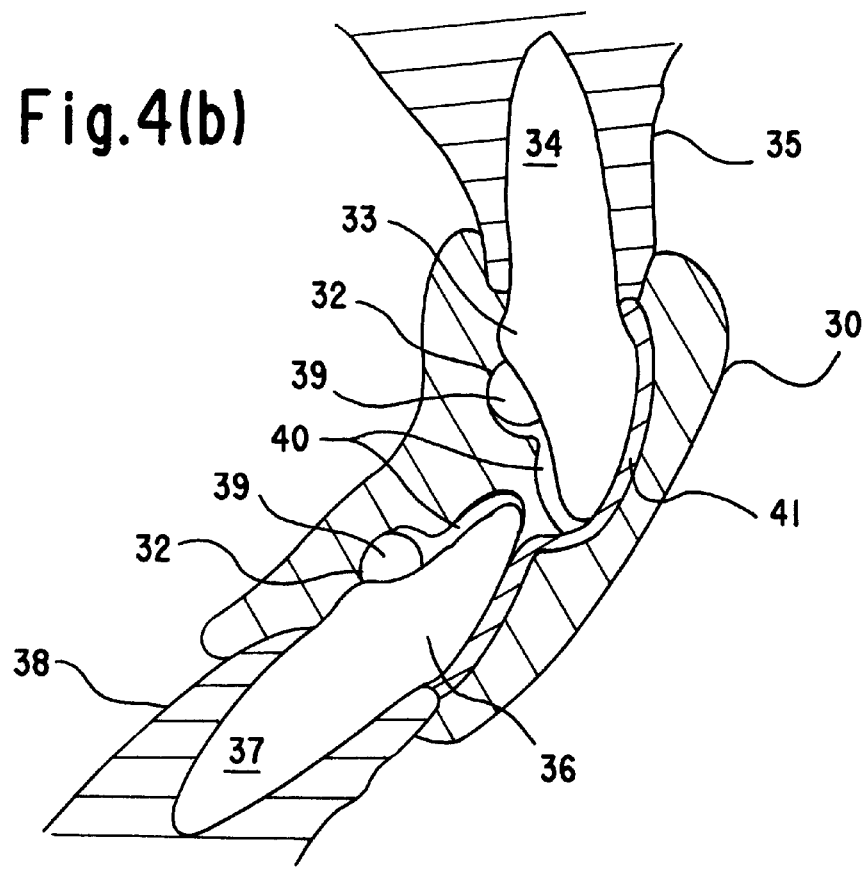
Figure 5A:
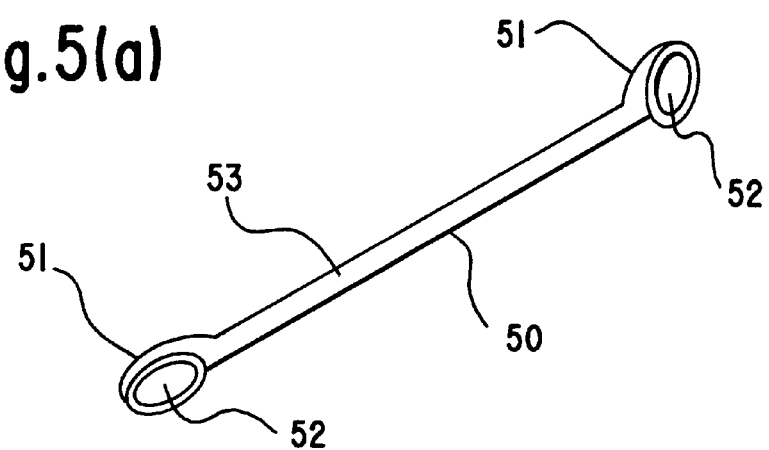
FIG. 5(a) is a squint showing a tool 50 necessary for the prior method to cure the open bite, (b) is a cross section of the tool 50, and (c) illustrates how to form the projection 39 on the tooth36.
Figure 5B:
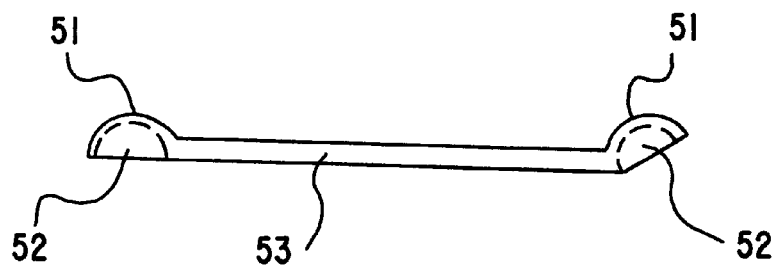
Figure 5C:
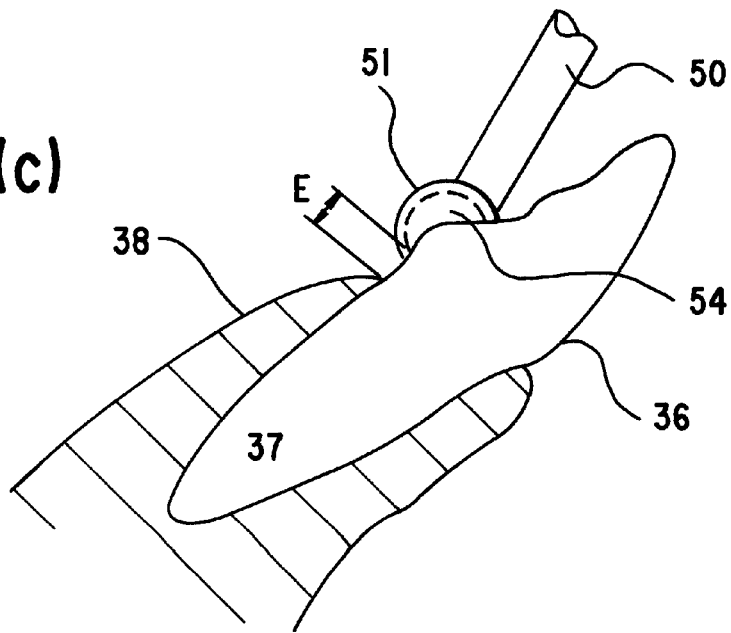

The size of the bite control point for the upper teeth should be a little bigger than that for the lower teeth. As shown in FIG. 3 in case of the latter embodiment, an open bite control for the upper front tooth is 2.0 mm to 5.0 mm in length and 1.5 mm to 5.0 mm in width whereas an open bite control for the lower is 1.5 mm to 4.5 mm in length and 1.5 mm to 3.0 mm in width. The dentist can apply twelve bite control points of different size, four of the twelve for incisors, four for canines, and four for molars, or may employ twenty four bite control points of various size for all the teeth to strengthen the tightness between the positioner and the bite control points.

The material of tooth color is preferred for the above embodiments1,3. The porcelain is not appropriate, however, as it is harder than tooth enamel giving a fear that the enamel may be rubbed and worn out, or cut and broken by the hardness of the porcelain. The rigid resin is a very suitable material, which is of tooth color and softer than enamel as well as hard enough to a certain degree.

The adhesive resin can be photo-synthetic type, MMA type, or no mix type. The photo-synthetic resin is easy to be handled as it remains loose unless it is exposed with irradiation so that the dentist can easily adjust the adhesion site and select the best spot before he/she irradiate a beam of ray. MMA type resin stiffens when it passes some time after the two materials are mixed and gives a good adhesive strength as long as the mixing ratio of materials is correct, although the operation is rather complicated. No mix type resin can be handled easier than MMA type resin because there is no need to mix the different materials, but the dentist has only one chance to decide the best spot and cannot adjust or move the adhesion site no more after the no mix type resin touches the tooth. While in the foregoing specification a detailed description of specific embodiments in case of treating open bite was set forth, this invention is also useful to treat other deseases for moving the teeth to the vertical direction.

What is claimed:

1. A bite control point, comprising:

a first surface to be adhered to a tooth;

a second surface with a convex shape, said convex shape having a slope at one edge which is gentler than that of the opposite side.

2. The bite control point as recited in claim 1, wherein said bite control point has a tear drop shape.

3. The bite control point as recited in claim 1, wherein said bite control point is made of rigid resin.

4. The bite control point as recited in claim 3, wherein said rigid resin is softer than enamel.

5. A method of forming a projection on a tooth surface, comprising the steps of:

preparing a ready made bite control point having a convex shape, said convex shape having a slope at one edge which is gentler than that of the opposite side;

etching an area for adhesion on a tooth side;

washing and drying said area;

putting an adhesive on a surface of said bite control point;

pressing said surface against said area on said tooth irradiating said adhesive.

6. The method as recited in claim 5, wherein said adhesive is a photo-synthetic type.

7. The method as recited in claim 6, wherein said a photo-synthetic type adhesive is an MMA type adhesive.

8. A method of attaching a bite control point to a tooth, comprising:

applying an adhesive on the surface of a pre-manufactured hard bite control point;

pressing the bite control point onto the surface of the tooth; and stiffening the adhesive.

9. The method of claim 8, wherein the adhesive is a photo-synthetic resin and the stiffening step includes irradiating the adhesive.

10. The method of claim 8, further comprising:

etching, washing and drying the surface of the tooth.

* * * * *